United States Patent
Jordan et al.

(10) Patent No.: US 6,787,324 B2
(45) Date of Patent: Sep. 7, 2004

(54) METHOD AND APPARATUS FOR DETECTING CONCEPTION IN ANIMALS

(75) Inventors: Nancy Tommye Jordan, Knoxville, TN (US); John Douglas Jordan, Knoxville, TN (US)

(73) Assignee: Concepto Diagnostics, Inc., Knoxville, TN (US)

( * ) Notice: Subject to any disclaimer, the term of this patent is extended or adjusted under 35 U.S.C. 154(b) by 133 days.

(21) Appl. No.: 09/764,826

(22) Filed: Jan. 17, 2001

(65) Prior Publication Data

US 2001/0024799 A1 Sep. 27, 2001

Related U.S. Application Data

(63) Continuation of application No. 09/016,995, filed on Feb. 2, 1998, now abandoned.

(51) Int. Cl.$^7$ .............................. G01N 33/53
(52) U.S. Cl. ................ 435/7.9; 435/7.1; 435/7.91; 435/7.92; 435/7.93; 435/7.94; 435/7.95; 436/510; 436/514; 436/518; 436/525; 436/526; 436/65; 436/814; 436/815; 436/817
(58) Field of Search ..................... 435/7.1, 7.9, 7.91, 435/7.92, 7.93, 7.94, 7.95; 436/514, 518, 525, 526, 65, 510, 814, 815, 817

(56) References Cited

U.S. PATENT DOCUMENTS 5,602,040 A 2/1997 May et al. .................. 436/514

FOREIGN PATENT DOCUMENTS

| EP | 0 291 194 | * 11/1988 |
| WO | 86/05498 | * 9/1986 |
| WO | WO 88/04779 | 6/1988 |
| WO | 99/39208 | * 8/1999 |

OTHER PUBLICATIONS

Morton et al., "Ovum Factor and Early Pregnancy Factor." Curr. Topics Dev. Biol. 23:73–92 (1987).
Trapani et al., "A re–examination of the association of 'early pregnancy factor' activity with fractions of heterogeneous molecular weight distribution in pregnancy sera." Early Pregnancy: Biology and Medicine 3(4):312–322 (Dec. 1997).
Zuo et al., "Isolation and Characterization of Early Pregnancy Factor." Chin. Med. Sci. J. 9(1):34–37 (1994).
Quinn et al., "Monoclonal antibodies to early pregnancy factor perturb tumour cell growth," Clin. Exp. Immunol. 80(1):100–108 (Apr. 1, 1990).
W.J.Sinosich, et al. "Placental Proteins in the Diagnosis and Evaluation of the Elusive Early Pregnancy" Obstetrical and Gynecological Survey, vol. 40. No. 5, 1985, pp. 273–282.
B.E. Rolfe, et al. "Early Pregnancy factor in an immunosuppressive contaminant of commercial preparations of human chorionic gonadotropgin" Clinical Exp. Immunology, 1983, vol. 51: pp. 45–52.
F.M. Clarke, et al. "Partial Characterisation of Early Pregnancy Factor in the Sheep", Journal of Reproductive Immunology 2 (1980) pp. 151–162.
F.M. Clarke, et al. "Detection and separation of two serum factors responsible for depression of lymphocyte activity in pregnancy" Clinical Exp. Immunology 1978, vol. 32:pp. 318–323.
F.P. Noonan, et al. "Early Pregnancy Factor is Immunosuppressive" Nature vol. 278, 1979, pp. 649–651.
Y. Cheng Smart, et al."Early Pregnancy Factor: Its Role in Mammalian Reproduction–Research Review" Pregnancy and Sterility, vol. 35. No 4. Apr. 1981, pp. 397–402.
A.C. Cavanagh,"Production in vitro of mouse early pregnancy factor and purification to homogeneity" J. Reprod. Fert. (1984) 71, pp. 581–592.
F.M. Clarke, et al."Early Pregnancy factor: Large scale isolation of rosette inhibition test–active polypeptides from ovine placental extracts"Journal of Reproductive Immunology, 10 (1987) 133–156.
W.R. Threlfall,(A) "Early Conception Assay Application To Diary Cow Pregnancy Determination" Soc. Theriogenol. Ann Conf., Aug. 12–14, 1993.
W.R. Threlfall,(B)"Immunosuppressive Early Pregnancy Factor (ISEPF) Determination For Pregnancy Diagnosis in Dairy Cows" 1994, Theriogenology 41:317.
K. A. Quinn and H. Morton "Effect of Monoclonal Antibodies to Early Pregnancy Factor (EPF) on the In Vivo Growth of Transplantable Murine Tumours" Cancer Immunology Immunotherapy vol. 34 1992 pp. 265–271.

* cited by examiner

Primary Examiner—Christopher L. Chin
(74) Attorney, Agent, or Firm—Needle & Rosenberg, P.C.

(57) ABSTRACT

The present invention provides antibodies which specifically bind early conception factor, which can be found in body fluids of animals including but not limited to the cow, cat, dog, horse, human, sheep, and pig. The invention provides methods for detecting conception or the absence of conception in an animal, the latter being recognized by the absence of early conception factor in a suitable body fluid collected from the animal. Apparati for detecting early conception factor in a body fluid from an animal comprising the antibodies which specifically bind early conception factor are also provided.

12 Claims, 1 Drawing Sheet

METHOD AND APPARATUS FOR DETECTING CONCEPTION IN ANIMALS

This is a 35 U.S.C. 111 application filed under 37 C.F.R. § 1.53(b) on Jan. 17, 2001, which is a continuation of and claims priority to U.S. Ser. No. 09/016,995, filed Feb. 2, 1998 now abandoned.

FIELD OF THE INVENTION

This invention relates to the field of detecting conception and/or implantation in animals, including humans, and apparati therefor.

BACKGROUND OF THE INVENTION

It has been a long-sought goal of physicians and veterinarians to have reliable diagnostic markers for conception, implantation and viable pregnancies, to help manage treatment of infertility and early pregnancy treatment. In humans, early pregnancy diagnosis based on placental protein markers is only routinely relied upon at 4 weeks after conception, and ultrasonic analysis is only reliably positive at 7–8 weeks gestation.

In the livestock industry, it is important to be able to identify animals that have not successfully conceived following breeding. For example, in the cattle industry at the present time, there is no way to identify such animals before 35–40 days after breeding, and the identification must be made by a veterinarian using palpation. Alternatively, ultrasound analysis can detect a developing embryo at 21 days. Veterinarian palpation is by far the most commonly used method, costing approximately $4 to $10 per test. The cost for an ultrasound analysis is prohibitive for routine farm management. In addition to the costs of these tests, the farmer suffers an additional and significant financial loss in having cows that have been bred but have not conceived, also referred to as "open" cows. The "open" cow costs the farmer an additional $4 to $10 dollars per day. The better milk producers are the hardest cows to breed, so while they are "open" the loss is even greater. Less than 50% of cows conceive on the first breeding. Due to this fact, the usual breeding program allows for 2½ semen straws per cow. If the time interval during which a cow is "open" can be shortened to days instead of months, this would substantially increase the overall calving rates.

A factor, named early pregnancy factor (EPF) or more recently immunosuppressive early pregnancy factor (ISEPF), has been detected in animals using a bioassay, and it is thought to be responsible for suppressing the maternal immune response against the embryo/fetus. Despite the demonstration of the activity through a bioassay, the literature presents several different MW forms for ISEPF. In mice, Clarke et al. (Clin Exp. Immunol. 32:318, 1978) reported an EPF of approximately 180,000 kD. In sheep, Clarke et al (J. Reprod. Immunol. 1980 Vol. 2:151) described the existence of multiple forms of EPF, including 20 kD, 50 kD, and 250–350 kD forms. In a 1987 paper from the same laboratory, Clarke et al describe the purification of a 12 kD EPF from the placenta of 12 weeks pregnant sheep (J. Reprod. Immunol. 1987 10:133–156). Cavanaugh described the purification of a 21 kD EPF from cultured ovaries and oviducts of mice, which is composed of three subunits, 10.5, 7.2 and 3.4 kD in size (J. Reprod. Fertil. 71:581, 1984). The factor has most recently been described as a glycoprotein of high molecular weight (Threlfall, 1993), but prior to this invention, a functionally pure preparation was not known.

An indirect bioassay for the ISEPF utilizes an in vitro, rosette inhibition assay described by Bach and Antoine (Nature 217:658 1968), which measures the ability of ISEPF to enhance the inhibition of rosette formation between T cells and heterologous erythrocytes induced by anti-lymphocyte serum (ALS). Both molecular weight components must be present to detect ISEPF in the rosette assay. It has been postulated that the ALS sterically hinders the binding of the erythrocytes in the assay; ISEPF enhances the inhibition by saturating some binding sites on the lymphocytes (Smart, Y C et al., Fertil. & Steril. 35:397, 1981). ISEPF has been found in the mouse (Morton et al., Nature 249:459 1974), rat (Heywood, L H et al. Australian Soc. for Reprod. Biol. 1979), human Morton, H. et al., Lancet 394 1977), sheep (Morton, H. et al. Res. in Vet. Sci. 26:261 1979), pig (Grewal, A S et al. Australian Soc. for Reprod. Biol. 1981), and cattle (Nancarrow et al. J. Reprod. & Fert. 57:385 1979). Noonan et al (Nature 278:629 and 649 1979) have described ISEPF as species non-specific.

Given the appearance of ISEPF very soon after mating, it is possible that ISEPF could be an excellent early marker for conception in animals. However, the rosette inhibition assay is technically difficult to perform, time-consuming, cumbersome and subject to numerous false-positive readings (Sinosich et al., 1985). To develop an ISEPF assay that is reproducible and not subject to a large number of false-positive signals, a substantially pure preparation of ISEPF is required. Prior to this invention, no protocols for the complete purification of a high molecular weight ISEPF have been reported.

There remains a need for a reliable assay to detect pregnancy as early as possible after conception and further to detect spontaneous abortion.

There is a need to be able to breed animals and determine, within 12–48 hours, whether the breeding has resulted in conception. In cattle, as an example, such non-conceiving cows could be recycled with injections of prostaglandin and inseminated again without the loss of thirty days. There is further a need to be able to enhance the ability of elite cows to implant at a higher rate.

SUMMARY OF THE INVENTION

The present invention provides a purified factor, herein referred to as the "early conception factor" or ECF, antibodies specific for ECF, and kits and apparatuses for detecting the presence or absence of ECF in fluid or tissue samples taken from animals. Methods for detecting conception within 12–48 hours of breeding/mating are described. Methods for detecting fetal death following conception and implantation are also provided. Means for enhancing embryonic implantation utilizing the ISEPF and the anti-ISEPF antibodies of this invention are also provided.

DETAILED DESCRIPTION OF THE INVENTION

Definitions

Figure 1:
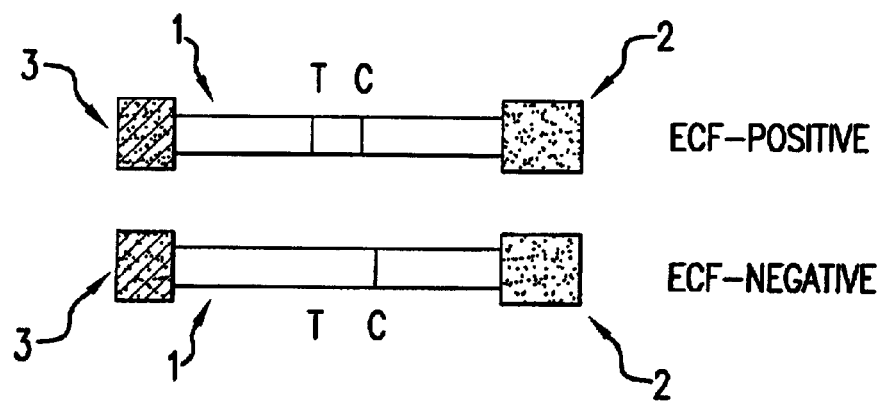
FIG. 1 is a schematic of the support of the present invention, showing 1) a support on which a sample containing ECF has been analyzed ("ECF-positive") and 2) a support on which a sample not containing ECF has been analyzed ("ECF-negative"); "T" marks the location of a band of test, or anti-ECF, antibodies; "C" marks the location of a band of control antibodies.

As used herein, "conception" can be used interchangeably with "fertilization".

As used herein, "a" can mean one or more than one.

As used herein, "purified" refers to a protein (polypeptide, peptide, etc.) that is sufficiently free of contaminants or cell components with which it normally occurs to distinguish it from the contaminants or other components of its natural environment. The purified protein can be homogenous, but need not be homogeneous. It must be sufficiently free of contaminants to be useful in a clinical or research setting, for example, in an assay for detecting antibodies to the protein.

Detailed Description

The present invention provides antibodies that specifically bind to purified ECF. The antibodies can be specifically reactive with a unique epitope of the antigen or they can also react with epitopes of other organisms. The term "bind" means capable of reacting or otherwise associating nonrandomly with an antigen. "Specifically bind", "specifically react with" or "specifically against" describe an antibody or other ligand that does not cross react substantially with any antigen other than the one specified, in this case, the purified ECF.

Preferably, the purified ECF has a molecular weight between 190,000 and 205,000 as measured by denaturing gel electrophoresis in a 4–15% gradient polyacrylamide gel, with appropriate MW standards including 20,000, 144,000 and 208,000 [Amersham Polyacryl® standards]. The glycoprotein ECF is obtained through an initial purification step that removes all non-glycoproteins. This step can be perchloric acid extraction. The resulting glycoprotein fraction can be used as described herein to produce antibodies and to treat animals, including humans. The ECF may be further purified by ion exchange chromatography, and further again by column chromatography, resulting in Fractions A1, A2, and B, as described in Example 1. These fractions are combined to produce a further purified ECF. ECF purified by one or more of the steps described in Example 1, and Fractions A1, A2 and B thereof, can be obtained from cows, cats, dogs, humans, horses, sheep and pigs.

The present invention provides antibodies that can recognize and bind ECF from cows, cats, dogs, humans, horses, sheep and pigs. The present antibodies can be of any isotype, e.g. IgG, IgM, or IgA types, from any animal, and they can be polyclonal, monoclonal, humanized, fully human or chimeric. The antibodies can be monovalent or divalent single chain antibodies. As contemplated herein, the antibody includes any ligand which binds the ECF, for example, an intact antibody, a fragment of an antibody or another reagent that has reactivity with the antigen. Antibodies raised against ECF from one species can be used to recognize and bind ECF from other species. Optimization of interspecies antigen-antibody reactions is performed according to protocols known in the art, including optimization of the ratio of antibody-antigen and the blocking proteins used to enhance specificity. Preferably, antibodies raised to the ECF from a given species are used to recognize and bind ECF from the same species.

The present invention provides a method of detecting the glycoprotein ECF using antibodies, by contacting a fluid or tissue sample from the subject with an amount of anti-ECF antibody specifically reactive with ECF, and detecting the reaction. It is contemplated that ECF can be detected in an intact form in the sample, or as fragments. The fluid sample of this method can comprise any body fluid which would contain ECF or a cell containing ECF, such as blood, plasma, serum, saliva and urine. Other possible examples of body fluids include sputum, mucus, gastric juice and the like. One method effective for the detection of ECF can, for example, be as follows: (1) bind the anti-ECF antibody to a support; (2) contact the bound antibody with a fluid or tissue sample containing ECF; (3) contact the above with a secondary antibody bound to a detectable moiety (e.g., horseradish peroxidase enzyme or alkaline phosphatase enzyme); (4) contact the above with the substrate for the enzyme; (5) contact the above with a color reagent; (6) observe color change. In a specific embodiment, washing steps are included between one or more of the steps listed above. The detectable moiety will allow visual detection of a precipitate or a color change, visual detection by microscopy, or automated detection by spectrometry, radiometric measurement or the like. Examples of detectable moieties include fluorescein and rhodamine (for fluorescence microscopy), horseradish peroxidase (for either light or electron microscopy and biochemical detection), biotin-streptavidin (for light or electron microscopy), colloidal gold (for precipitate formation) and alkaline phosphatase (for biochemical detection by color change). The detection methods and moieties used can be selected, for example, from the list above or other suitable examples by the standard criteria applied to such selections (James W. Goding, *Monoclonal Antibodies: Principles and Practice*, Academic Press, 1983; and Harlow and Lane, *Antibodies; A Laboratory Manual*, Cold Spring Harbor Laboratory, Cold Spring Harbor, N.Y., 1988).

A specific embodiment of this invention for detecting ECF involves the use of a "dipstick" assay in which a strip (the "dipstick") is prepared with anti-ECF antibodies immobilized on the strip in a sharp band at a location spacially separated from the location for loading sample. At the sample loading location, anti-ECF antibodies labeled with a detectable moiety are deposited. Then, a) a test fluid is added to the sample loading pad; b) the ECF in the test fluid binds to the anti-ECF antibodies, and this complex is wicked along the strip by capillary flow until it contacts the immobilized anti-ISEPF antibody band; and c) ECF:anti-ECF antibody complexes are concentrated at the band, allowing visualization of the detectable moiety, by any of the methods described above. In a further embodiment of this invention, a second band of antibodies can be immobilized on the strip, on the side distal to the sample loading band. The antibodies of this second band are chosen to recognize the immunoglobulin of the animal in which the anti-ECF antibodies were produced, e.g. anti-goat IgG. This second band serves as an internal, positive control for the dipstick assay to demonstrate that the dipstick is working properly. The amount of anti-ISEPF antibodies immobilized at the first band is controlled so that enough ECF:anti-ECF antibody complex will move through the first band location to contact the anti-goat IgG antibodies.

The present invention provides a method of detecting conception or implantation in an animal comprising detecting the presence of ECF in samples taken from a mated female animal. The type of sample taken will depend on the species of animal being tested, but serum, urine or milk samples are preferred. Saliva and vaginal secretions can also be used. The sample can be used without further processing or it can be processed by dilution in a fluid, such as a blocking solution to limit non-specific binding. Examples of blocking solutions include SeaBlock (East Coast Biologicals, New Brerwich, Me.) mixed with 1% newborn calf serum and 10 mM Tris with 2% Tween-20.

The present invention further provides a method for detecting the absence of conception in an animal within 12–48 hours of mating comprising determining the presence or absence of ECF, the absence of ECF indicating the absence of conception.

The present invention provides methods for detecting spontaneous abortions in pregnant animals by monitoring the level of ECF after mating, e.g. from less than one day to 48 days. Preferably, the levels of ECF are monitored periodically following conception and/or implantation. In humans, such monitoring can also be used to minimize the use of abortion-inducing drugs, e.g. RU-486, by indicating whether conception and implantation have occurred following mating.

The present invention can be used to enhance the likelihood of implantation or conception in animals, including humans, and to minimize the chances for abortion. Low levels of ECF are correlated with a lower likelihood of conception or implantation, while higher ECF levels are a good predictor of a high likelihood of conception, implantation and maintained pregancy. Thus, animals could be provided with additional ECF, most likely through intravenous administration, to bring their levels of ECF into the appropriate ranges for conception, implantation and pregnancy maintenance.

The present invention provides apparati for use in detecting the presence of ECF comprising a support on which antibodies to ECF are present. In one embodiment (FIG. 1), the support (1) comprises a strip made of material along which fluid can flow. At one end of the strip, sample fluid is introduced, and the fluid flows along the support and contacts antibodies to ECF. In a specific embodiment, a wicking aid (2), such as Whatman CHO-17, is attached to the non-sample end of the strip to enhance fluid flow. In a specific embodiment, the location for sample introduction includes an absorbent pad (3), which can be made of a glass fiber material, Whatman FO-75, or any other suitable material.

Figure 2A:
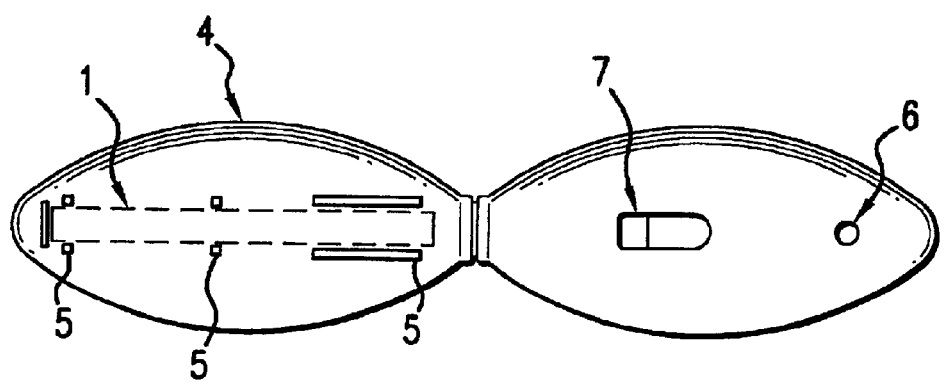
FIG. 2 is a schematic of a body in contact with a support of the present invention, shown in both the open and closed positions.
Figure 2B:
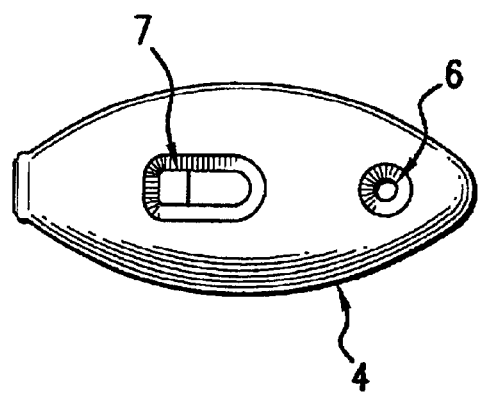

The present invention provides apparati for use in detecting the presence of ECF comprising a body in contact with a support on which antibodies to ECF are present. The body can be made from different types of materials, e.g plastic, metal, or cardboard, and it can be of any shape that will accomodate the support. A specific embodiment (FIG. 2) of the body (4) is a football-shaped compact, 4 to 10 cm long, hinged at one end, with guides (5) to secure the support and one opening (6) for introduction of the sample and another opening (7) for viewing the antibody-antigen reaction. Another specific embodiment is a rectangularly shaped box with a bottom and top, (2–3)×(4–10) cm. The support can be any material to which antibodies can be bound. Different types of antibodies may bind better to one support than another, as is well understood in the art. As an example, IgA monoclonal antibodies do not bind well to most membranes. Nevertheless, having determined a method for accomplishing this, the present invention can utilize IgA antibodies.

In one embodiment of the apparatus, the antibodies to ECF are monoclonal IgAs, and the sample pad is a glass fiber material. In a specific embodiment, the absorbent sample pad is made from Whatman FO-75. In a specific embodiment of the apparatus, the antibodies to ECF are polyclonal, and the support is a 5 micron nitrocellulose membrane. In a specific embodiment, the nitrocellulose membrane is Whatman 5 $\mu$M. Other membranes, currently available or later developed, can also be used. The absorbent sample pad and any wicking aid can be disposed atop the support material, for example the nitrocellulose membrane. Alternatively, the absorbent sample pad and a wicking aid can be placed so that their ends abut the ends of the support, such as the nitrocellulose membrane.

In one embodiment of the apparatus, the support will have anti-ECF antibodies placed at two, spacially separated locations. A fluid containing the test sample from an animal is introduced to the support, and the support wicks the fluid so that it first contacts the location on the support where labeled antibodies have been deposited, and then continues to wick along the support to contact the second location wherein antibodies are bound. Anti-ECF polyclonal antibodies can be used at both locations, or any combination of anti-ECF monoclonal and polyclonal antibodies at the two locations can be used. For example, labeled anti-ECF monoclonal antibodies are placed at one location on the support, anti-ECF polyclonal antibodies are bound to another location, and the test sample is introduced at the location wherein the monoclonal antibodies have been placed. In another embodiment, labeled anti-ECF polyclonal antibodies are placed at the location where the sample is introduced, and anti-ECF monoclonal antibodies are immobilized at the second location. Anti-ECF monoclonal antibodies recognizing different epitopes can be used at both locations.

The apparatus can further include means for directing the sample-containing fluid to the chosen location on the support. In a further embodiment, a blocking solution, as described herein, can be added after the sample is placed on the support.

Throughout this application, various publications are referenced. The disclosures of these publications in their entireties are hereby incorporated by reference into this application in order to more fully dsecribe the state of the art to which this invention pertains.

EXAMPLES

Example 1

Purification of ECF

Serum was collected from cows at 12–48 hours after breeding in volumes greater than 250 ml and frozen until pregnancy was confirmed in 45 days. When serum was approved for ECF extraction, through confirmation of pregnancy by other means, it was thawed at room temperature. Equal volumes of a dilute perchloric acid solution (70% perchloric acid diluted in a ratio of 1 ml per 50 ml distilled water) and serum were mixed using a magnetic stirrer. The mixture was kept in an ice bath with constant stirring for 1 hour. The mixture was then centrifuged for 30 minutes at 2000 g using a refrigerated centrifuge. The resulting supernatant was dialyzed for 72 hours against distilled water, then checked for the presence of ECF by immunological documentation.

Dialyzed supernatant, buffered to pH 7.4 with sodium phosphates, containing ECF was further purified using a highly purified cellulose powder containing diethylaminoethyl (DEAE) exchange groups equilibrated in 0.025M sodium phosphate buffer pH 7.4. The non-absorbed fraction from the DEAE powder was collected as Fraction A. The material in the supernatant that bound to the DEAE column was eluted using 0.05M Sodium Phosphate, 0.9% sodium chloride pH 7.4 and collected as Fraction B. Fractions A and B were each dialyzed against distilled water.

Fraction A was then further purified by passing it over a Sepharose 4B with 0.05M Tris HCL buffer pH 7.4, and collecting two peaks, labeled Fraction A1 and Fraction A2, which were then recombined to reconstitute Fraction A.

The two ECF fractions, A (reconstituted as above) and B, and a combination of equal milligrams of Fractions A and B, were each diluted to 1 milligram per ml in normal saline. These three preparations were used to immunize three separate graded goats for the production of antibodies. The three goats' antiserum were tested against each of the three immunizing preparations. For example, Goat No. 20, which was immunized with the combination of Fraction A and Fraction B, showed strong immunological reactivity against all three of the immunizing antigens.

Example 2
Production of Anti-ECF Polyclonal Antibodies

Graded goats were immunized with the purified ECF fractions A and B from Example 1, which were combined and diluted to 1 mg/ml.

Eight primary injections of antigen using Freund's complete adjuvant were given to each goat. A typical immunizing antigen preparation contained 20 ml of reconstituted Fraction A and Fraction B (both prepared as described in Example 1) at 1 mg/ml and 20 milliters of Freund's Complete Adjuvant. Two (2) milliters of this preparation were removed and homogenized to less than 1 milliter which was then injected into the muscle of the goat. Injections were given twice a week, three days apart. Eight days following the eighth injection, the goats were bled and the antibodies harvested from the blood. The antibodies were tested for activity against purified ECF. Those animals that tested positive were subsequently given monthly booster injections, and were bled eight days after each booster injection to provide a steady supply of antiserum.

To increase the specificity of the antiserum so produced, each serum collection was absorbed with pooled normal human serum and serum from non-immunized cows until no lines were visible in Ouchterlony Gel Diffusion studies. This pre-absorbed antiserum was further purified using sodium sulfate fractionation. The resulting antibody preparations were then used for the development of a hemagglutination-inhibition assay and an enzyme immunoassay. The antibodies were also further purified using a Procept A (Bioprocessing Ltd., Durham, United Kingdom) chromatographic column, eluted with phosphate buffered saline at pH 7.4, and these antibodies were used in the dip-stick assay.

Example 3
Production of Anti-ECF Monoclonal Antibodies

Balb C mice were used for immunization using the immunizing preparations described in Example 2. The same immunization schedule as used for the goats was followed for the mice, except that two days following the last injection, the fusion of the mouse spleen cells with SP2/0-Ag melanoma cells (available from American Type Culture Collection) using 30% polyethyleneglycol in RPMI 1640 medium was performed. Standard maintenance of hybridoma cells in hypoxanthine, aminopterin, and thymidine (HAT)-containing medium was followed (Goding, 1983; and Harlow and Lane, 1988). The antibody producing cells with the strongest titer were identified using hemagglutination procedures with red blood cells that were coated with ECF, prepared following standard procedures known in the art.

Selected hybridoma cells were propagated for the production of monoclonal antibodies. Cloning of a specific hybridoma cell line was done by limiting dilution in fluid phase and semisolid agarose techniques. The anti-ECF antibody producing clones were maintained and grown in volume using HAT-containing DMEM (Dulbecco's modified Eagle's medium), using protocols known in the art (Harlow and Lane, 1988).

An anti-ECF monoclonal antibody selected by these procedures was isotyped and documented to be an IgA. It was shown to react with various preparations of ECF antigens by Western blot analyses. This monoclonal antibody was coupled to colloidal gold using procedures known in the art (e.g. Julian Beesley, *Colloidal Gold*, Oxford Press, 1989)

Example 4
Construction of an Assay Kit for Determining Conception Status

A kit was constructed using anti-ECF polyclonal antibodies described in Example 2 bound to a 4.5×0.5 centimeter (cm) strip of Whatman's 5 micron nitrocellulose membrane. Anti-ECF monoclonal antibodies, as described in Example 3, were coupled to colloidal gold to form a conjugate and deposited on a 2.5 cm×0.5 pad of Whatman's OF-75 material.

The kit was assembled as a lateral flow device by placing the two antibody-containing strips end-to-end as a 7 cm strip, with the animal test sample to be introduced to the FO75 pad, i.e. the "sample end". A second pad, made from CHO-17 glass fiber material, was placed at the other end (i.e. the non-sample end) to aid in the wicking of fluid from the sample end through the nitrocellulose membrane strip. The anti-ECF polyclonal antibodies were bound to the membrane in a "Test" band (approximately 0.1 cm in width) located approximately 3.4 cm from the sample end of the strip. A control goat IgG antibody (Sigma, St. Louis, Mo.) was bound in a similarly sized "Control" band located approximately 0.5 cm from the anti-ECF polyclonal antibodies, on the side of this band distal from the sample end.

Example 5
Performing the ECF Assay for "Open" Cows

A serum sample from a cow being tested was introduced as a drop to the strip kit of Example 4 at the sample end of the strip, approximately 1 cm from the end of the strip. Approximately 2–8 drops of blocking buffer is added directly on top of the serum sample, and the liquid is allowed to wick along the strip to the two areas bound with antibodies. The presence of a single line on the strip (which would be located at the control band) indicates that the cow is "open", i.e. the cow has not conceived. The presence of two lines on the strip, located at each of the control and test bands, indicates a cow that has conceived.

The assay was performed on 153 cows that had been artificially inseminated, and the results of the ECF assay were compared to the results from veterinary palpation. Of 65 animals shown to be pregnant by veterinary palpation, 53 were positive in the ECF assay. Of 89 animals determined not to be pregnant by palpation, 45 were negative in the ECF assay.

Example 6
Assay for ECF in Humans

Samples were collected from patients who were artificially inseminated. Samples were assayed for the presence of ECF using a urease-anti-ECF conjugate. The following data was collected:

| Patient No. | Sampling Time after insemination (in days) | | | | Pregnant? |
| --- | --- | --- | --- | --- | --- |
| | 0.25 | 2.0 | 6.0 | 12.0 | |
| 1 | .358 | .120 | .100 | .100 | no |
| 2 | .114 | .095 | .094 | .091 | no |
| 3 | .103 | .099 | .093 | .098 | no |
| 4 | .103 | .096 | .100 | .095 | no |
| 5 | .070 | .079 | .052 | .088 | no |

-continued

| | Sampling Time after insemination (in days) | | | | |
|---|---|---|---|---|---|
| Patient No. | 0.25 | 2.0 | 6.0 | 12.0 | Pregnant? |
| 6 | .104 | .096 | .081 | .108 | no |
| 7 | .301 | .159 | .105 | .111 | no |
| 8 | .104 | .106 | .094 | .101 | no |
| 9 | .102 | .098 | .092 | .058 | no |
| 10 | .075 | .085 | .091 | .050 | no |
| 11 | .075 | .082 | .078 | .087 | no |
| 12 | .073 | .076 | .081 | .096 | no |
| 13 | .079 | .081 | .078 | .078 | no |
| 14 | 1.657 | 1.691 | 1.674 | 1.557 | yes |
| 15 | 1.660 | 1.690 | 1.708 | 1.577 | yes |
| 16 | .087 | .070 | .087 | .088 | no |
| 17 | .074 | .078 | .075 | .077 | no |
| 18 | .085 | .077 | .074 | .074 | no |
| 19 | .087 | .081 | .075 | .030 | no |
| 20 | .082 | .077 | .079 | .096 | no |
| 21 | .084 | .079 | .074 | .075 | no |
| 22 | .083 | .078 | .078 | .077 | yes* |
| 23 | .087 | .088 | .090 | .078 | no |
| 24 | .077 | .074 | .078 | .080 | no |

Patient No. 15 aborted at 3 months.
*Patient No. 22 aborted at 6 weeks.

Although the present invention has been described with reference to specific details of certain embodiments thereof, it is not intended that such details should be regarded as limitations upon the scope of the invention except as and to the extent that they are included in the accompanying claims.

What is claimed is:

1. A method for detecting conception in an animal comprising:
    a) contacting a fluid or tissue sample from the animal with an antibody that specifically binds early conception factor under conditions whereby the antibody can bind to early conception factor, and wherein earl conception factor has a molecular weight from about 190,000 daltons to about 205,000 daltons; and
    b) detecting binding of the antibody to the sample, wherein detecting the binding indicates the presence of early conception factor in the sample and conception in the animal.

2. The method of claim 1, wherein the body fluid is blood, plasma or serum.

3. The method of claim 1, wherein the body fluid is urine.

4. The method of claim 1, wherein the body fluid is milk.

5. The method of claim 1, wherein the antibody that specifically binds early conception factor is conjugated to a detectable moiety, and wherein after step b), the sample is washed, and the antibody bound to early conception factor is detected by adding a substrate or inducer, and changes in the substrate or inducer are monitored.

6. The method of claim 5 wherein the antibody that specifically binds early conception factor is conjugated to a moiety selected from the group consisting of alkaline phosphatase, horseradish peroxidase, colloidal gold, and urease.

7. A method for detecting early conception factor in an animal comprising the steps of:
    a) contacting a sample from the animal with an antibody that specifically binds early conception factor under conditions hereby the antibody can bind early conception factor protein present in the sample and wherein early conception factor has a molecular weight from about 190,000 daltons to about 205,000 daltons; and
    b) detecting binding of the antibody to early conception factor, wherein the binding indicates the presence of early conception factor in the animal.

8. The method of claim 7, wherein sample is blood, plasma or serum.

9. The method of claim 7, wherein the sample is urine.

10. The method of claim 7, wherein the sample is milk.

11. The method of claim 7, wherein the antibody that specifically binds early conception factor is conjugated to detectable moiety, and wherein after step b), the sample is washed, and the antibody bound to early conception factor is detected by adding a substrate or inducer, and changes in the substrate or inducer are monitored.

12. The method of claim 11 wherein the antibody that specifically binds early conception factor is conjugated to a moiety selected from the group consisting of alkaline phosphatase, horseradish peroxidase, colloidal gold, and urease.

* * * * *